(12) United States Patent
Shafee et al.

(10) Patent No.: US 9,995,730 B2
(45) Date of Patent: Jun. 12, 2018

(54) HYPOXIA INDUCIBLE FACTOR (HIF) ACTIVITY REPORTER CELL LINE

(71) Applicant: Universiti Putra Malaysia (UPM), Serdang, Selangor (MY)

(72) Inventors: Norazizah Shafee, Selangor (MY); Eric J. Stanbridge, Selangor (MY); Khatijah Yusoff, Selangor (MY); Sien-Yei Liew, Selangor (MY)

(73) Assignee: UNIVERSITI PUTRA MALAYSIA, Selangor (MY)

( * ) Notice: Subject to any disclaimer, the term of this patent is extended or adjusted under 35 U.S.C. 154(b) by 0 days. days.

(21) Appl. No.: 14/415,064

(22) PCT Filed: Jan. 29, 2013

(86) PCT No.: PCT/MY2013/000013
§ 371 (c)(1),
(2) Date: Jan. 15, 2015

(87) PCT Pub. No.: WO2014/021705
PCT Pub. Date: Feb. 6, 2014

(65) Prior Publication Data
US 2015/0168376 A1    Jun. 18, 2015

(30) Foreign Application Priority Data
Aug. 2, 2012 (MY) .......................... PI 2012003492

(51) Int. Cl.
*C12N 15/85* (2006.01)
*G01N 33/50* (2006.01)
*C12Q 1/66* (2006.01)

(52) U.S. Cl.
CPC .......... *G01N 33/5011* (2013.01); *C12Q 1/66* (2013.01); *G01N 33/5023* (2013.01); *G01N 2333/505* (2013.01); *G01N 2500/04* (2013.01); *G01N 2500/10* (2013.01); *G01N 2800/7038* (2013.01)

(58) Field of Classification Search
None
See application file for complete search history.

(56) References Cited

U.S. PATENT DOCUMENTS 5,834,306 A * 11/1998 Webster ................. C07K 14/47
435/320.1
2005/0037390 A1  2/2005 King et al.

OTHER PUBLICATIONS

Krishnamurthy et al (The Journal of Biological Chemistry, vol. 279, No. 23, pp. 24218-24225).*
Kaluz, Stefan et al., "Rational design of minimal hypoxia-inducible enhancers," *Biochem Biophys Res Commun.*, 2008, 370(4):613-618.
Liew, Sien-Yei et al., "Hypoxia affects cellular responses to plant extracts," *Journal of Ethnopharmacology*, 2012, 144:453-456.
Shibata, Toru et al., "Enhancement of Gene Expression Under Hypoxic Conditions Using Fragments of the Human Vascular Endothelial Growth Factor and the Erythropoietin Genes," *Int. J. Radiation Oncology Biol. Phys.*, 1998, 42(4):913-916.
Wood, S. Morwenna et al., "Selection and Analysis of a Mutant Cell Line Defective in the Hypoxia-inducible Factor-1 α-Subunit (HIF-1α): Characterization of HIF-1α-Dependent and -Independent Hypoxia-Inducible Gene Expression*," *The Journal of Biological Chemistry*, 1998, 273(14):8360-8368.
Zheng, Ken Y.Z. et al., "The expression of erythropoietin triggered by Danggui Buxue Tang, a Chinese herbal decoction prepared from Radix Astragali and Radix Angelicae Sinensis, is mediated by the hypoxia-inducible factor in cultured HEK293T cells," *Journal of Ethnopharmacology*, 2010, 132:259-267.

* cited by examiner

*Primary Examiner* — Celine Qian
(74) *Attorney, Agent, or Firm* — Saliwanchik, Lloyd & Eisenschenk

(57) ABSTRACT

The present invention relates to the construction of a new hypoxia inducible factor (HIF) responsive reporter gene construct, the genetic constructs and vectors containing the same. Further, the present invention relates to a stable cell line comprising the HIF responsive reporter construct, as well as methods and uses of the inventive constructs and cell lines to identify modulators of HIF activity.

4 Claims, 5 Drawing Sheets

HYPOXIA INDUCIBLE FACTOR (HIF) ACTIVITY REPORTER CELL LINE

CROSS REFERENCE TO A RELATED APPLICATION

This application is a National Stage Application of International Application Number PCT/MY2013/000013, filed Jan. 29, 2013; which claims priority to Malaysian Application No. PI 2012003492, filed Aug. 2, 2012; which are incorporated herein by reference in their entirety.

FIELD OF THE INVENTION

The present invention relates to the construction of a new hypoxia inducible factor (HIF) responsive reporter gene construct, the genetic constructs and vectors containing the same. Further, the present invention relates to a stable cell line comprising the HIF responsive reporter construct, as well as methods and uses of the inventive constructs and cell lines to identify modulators of HIF activity.

BACKGROUND OF THE INVENTION

An early response to tissue hypoxia is induction of hypoxia inducible factor (HIF), a basic helix-loop-helix transcriptional activator that mediates changes in gene expression in response to changes in cellular oxygen concentration. Hypoxia, a state of reduced oxygen, can occur when the lungs are compromised or blood flow is reduced. Ischemia, reduction in blood flow, can be caused by the obstruction of an artery or vein by a blood clot (thrombus) or by any foreign circulating matter (embolus), or by a vascular disorder such as atherosclerosis.

Modern drug discovery has been accelerated by the use of cell-based assays. Currently, these assays are utilized for lead identification, drug dose optimization as well as target validation. The use of small-scale yet high-throughput techniques makes these cell-based assays more efficient and cheap for drug screening. These assays are preferred over other in-vitro methods since they give direct cellular functional responses to the drug target of interest. This allows for clearer understanding of physiological and pharmacological responses to the target.

Currently, demand for assays to quantitate HIF activities is tremendous. This is due to the fact that besides being involved in various cellular regulations from proliferation, apoptosis to cancer development, HIF has also been shown to be involved in stem cell renewal and differentiation (Keith and Simon, 2007). The boost of stem cell research in the last decade has raised the need for a more robust cell-based assay system to measure HIF activities particularly in HIF-related drug screening. Unfortunately, the systems that are currently available are very inefficient, costly, time consuming and most importantly provide limited sensitivity. The choice of cell lines is also restrictive.

Development of cell-based HIF assay systems have been previously reported (Woldemichael et al., 2006; Ji et al., 2008). However, up to now only two HIF assay cell lines are commercially available. One is from Invitrogen, named 'CellSensor® HRE-bla ME-180 Cell Line' (cat# K1644). The other is from Panomics, under the name 'Stable Cell Line: NIH3T3/HIF-luc' (cat # RC0017). SABiosciences, a Qiagen company, also sells HIF assay kits, however, their kits are in the form of ready-to-transduce lentiviral particles or ready-to-transfect plasmids. Recently, the Emory University and The University of Rochester have also reported developments of reporter cell lines for HIF activity assay in their technology transfer catalogs. The signal ratio of hypoxia versus normoxia for the commercially-available CellSensor HRE-bla (Invitrogen) is just 13 fold. While another system developed by Li et al., (2008), only gave 14-fold difference. In the case of an unfavourable signal to noise ratio in cell based assays, such low inducibilities might render the application of these systems in a high throughput format for drug screening impossible.

In view of the above known reporter constructs of HIF activity it is an object of the present invention to provide an HIF responsive system which shows higher inducibility and specificity to HIF activation, specifically in response to hypoxia. Therefore, a further object of the present invention is to provide novel means for drug screening of modulators of HIF response, for example systems that are suitable to be applied in a high throughput format.

The above problem is solved in a first aspect by a gene construct which has a reporter gene integrated under the control of a hypoxia inducible factor (HIF) responsive promoter, wherein the HIF responsive promoter comprises at least one hypoxia-response element (HRE) derived from an erythropoietin (EPO) gene.

A gene construct according to the present invention shall refer to a nucleic acid molecule composed of several functional elements to allow for the expression of a reporter gene. The nucleic acid used in the context of the present invention can be single or double stranded; can be DNA or other nucleic acid molecules known in the art.

A promoter is a nucleic acid sequence that directs the transcription of a structural gene. Typically a promoter is located in the 5' region of a gene, proximal to the transcriptional start site of a structural gene. The promoter of the invention comprises HRE element(s). Additionally, the promoter may include upstream elements. Such elements include UARs and optionally, other nucleic acid sequences that affect transcription of a structural gene such as a synthetic upstream element or an enhancer.

A core promoter or minimal promoter contains the essential nucleotide sequences for expression of the operable linked coding sequence, including the TATA box and start of transcription. By this definition, a core promoter may or may not have detectable activity in the absence of specific sequences that may enhance the activity or confer tissue specific activity.

In one embodiment of the present invention, the promoter of the gene construct comprises at least 4 HREs. The HREs in the construct are located preferably in a tandem repeat, most preferably wherein the promoter is upstream of the reporter gene. Upstream of the reporter gene shall mean that the promoter sequence is located 5' of the start codon of the reporter gene, even more preferably wherein the HRE of the invention are located 5' of a TATA box upstream of the start codon of the reporter gene. In a preferred embodiment the construct of the present invention is depicted schematically in FIG. 2.

Another preferred embodiment of the present invention relates to a construct wherein the HRE is derived from human the EPO promoter region.

In the context of the present invention any reporter gene known to the person of skill in the art may be used and operably linked to the above described HRE element. Commonly used reporter genes that induce visually identifiable characteristics usually involve fluorescent and luminescent proteins. Examples include the gene that encodes jellyfish green fluorescent protein (GFP), which causes cells that express it to glow green under blue light, the enzyme luciferase, which catalyzes a reaction with luciferin to produce light, and the red fluorescent protein from the gene dsRed. A common reporter in bacteria is the *E. coli* lacZ gene, which encodes the protein beta-galactosidase. This enzyme causes bacteria expressing the gene to appear blue when grown on a medium that contains the substrate analog X-gal. An example of a selectable-marker which is also a reporter in bacteria is the chloramphenicol acetyltransferase (CAT) gene, which confers resistance to the antibiotic chloramphenicol. Similar markers are known to work for vertebrate cell lines. Most preferred in the context of the present invention is the use of a luciferase, most preferably wherein the reporter gene is a firefly luciferase.

In another preferred embodiment the present invention relates to a gene construct comprising the exact 4 times the sequence of the human EPO HRE upstream of a TATA-box and the reporter gene.

The above object of the present invention is solved in another aspect by a vector comprising the gene construct or nucleic acid sequence as described herein. A vector within the meaning of the present invention is a nucleic acid that is capable of being introduced into a cell. It is preferred that the proteins encoded by the introduced nucleic acids are expressed within the cell upon introduction of the vector. In a preferred embodiment, the vector of the present invention comprises recombinant vectors, plasmids, phagemids, phages, cosmids, viruses, in particular but not limited to virus-derived amplicon vectors.

The object of the present invention is furthermore solved by a cell line that comprises the gene construct or the vector, as described in the various embodiments of the present invention. The gene construct or vector may be transiently or stably transfected (or transduced) into said cells. It is preferred that the cells used for transfection are vertebrate, most preferably mammalian or human cells.

In one embodiment it is preferred that the cell line of the invention comprises a stably integrated gene construct and/or vector of the invention.

In a most preferred embodiment the cell line is an osteosarcoma cell line, preferably wherein the cell line is Saos-2.

In the present invention, the inventors used the human osteosarcoma cell line, Saos-2, while others have used the ME-180 cervical carcinoma cell line (Invitrogen) and the NIH-3T3 mouse embryo fibroblast cell line (Panomics). A rat glioma cell line was also used (Research Tools catalog, Emory University). In the present study several human cancer cell lines were screened, including breast adenocarcinoma MCF7, cervical carcinoma HeLa, renal carcinoma 786-O and osteosarcoma Saos-2 cell lines. Luciferase signals that were produced by our reporter construct upon hypoxia induction were highest in the Saos-2 cells. Based on these novel findings, the development of a stable hypoxia reporter construct cell line, using the Saos-2, was conducted.

The problem posed is furthermore solved by a method for assaying HIF response in a cell, comprising the steps of:
 a. introducing a gene construct according to any one of claims 2 and 4 into said cell,
 b. incubating said cell in hypoxic conditions,
 c. optionally, incubating a control cell in normoxic conditions, and
 d. ensuring the reporter gene expression corresponds to the HIF response in said cell.

In this aspect it is in another embodiment preferred that said cell is an osteosarcoma cell.

Furthermore, embodiments of the invention relate to the above method, wherein the gene construct is transduced or transfected into said cell, preferably wherein said gene construct is stably transduced or transfected into said cells.

In the context of the present invention, the term "hypoxia" shall refer to an oxygen ($O_2$) concentration in the atmosphere that is between 0 and 5% $O_2$, preferably between 0.01 and 1% $O_2$, more preferably between 0.01 and 0.3% $O_2$. In a most preferred embodiment hypoxia refers to a concentration of oxygen of about 0.3% $O_2$.

On the other hand, in the context of the present invention the term "normoxia" shall denote a concentration of oxygen of between 5 and 21% $O_2$, preferably between 10 and 21% $O_2$, more preferably between 10 and 20% $O_2$. In a most preferred embodiment the "normoxia" refers to a normal atmospheric oxygen concentration.

The problem of the present invention is furthermore solved by a screening method for identifying modulators of HIF response comprising, performing the above method of the invention, and contacting said cells with a compound which is suspected to be a modulator of HIF signaling, wherein an increase in reporter gene expression compared to an untreated control indicates that the compound is an agonist of HIF response, and wherein a decrease of reporter gene expression compared to an untreated control indicates that the compound is an antagonist of HIF response.

Suitable test compounds for use in the context of the present invention are small molecules comprised in compound libraries. Alternatively, proteins or peptides can be used.

Also nucleic acid molecules can be used as candidate compounds for the herein described, screening methods. Of these, inhibitory RNAs are of particular interest. This may be antagomirs, siRNAs, dsRNAs or antisense RNAs. Inhibitors RNA molecules are commercially available in libraries suitable for a screening approach in high throughput format.

Furthermore, the present invention provides a compound that modulates hypoxia response obtained by the above screening method.

In another aspect, the present invention relates to a kit for testing HIF response in a cell, comprising a gene construct, or a vector, or a cell according to any of the herein described embodiments of the invention.

Optionally the kit of the invention may include manual instructions how to perform the methods of the present invention and/or buffers and/or solutions for performing a HIF response test.

Furthermore, the invention relates to the use of the inventive material as shown herein, specifically the inventive gene construct, the vector, the cell or the kit, in a screening method for modulators of HIF mediated response or hypoxia induced response.

While the present invention has been described with specificity in accordance with certain of its preferred embodiments, the following examples serve only to illustrate the invention and are not intended to limit the invention within the principles and scope of the broadest interpretations and equivalent configurations thereof.

DETAILED DESCRIPTION OF THE INVENTION

EXAMPLE 1

Figure 1:
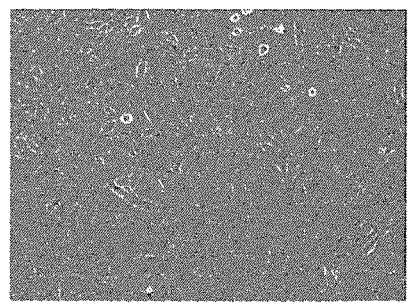
FIG. 1: Saos-2 cells obtained from the ATCC displayed a typical epithelioid morphology.

HIF Reporter Gene Construct and Stably Transfected Cells

Establishment of this HIF cell-based screening assay was achieved by an initial co-transfection of the 4XEPO-HRE-FLuc plasmid and the pcDNA3 plasmid (Invitrogen) carrying an antibiotic resistant gene, into the Saos-2 osteosarcoma cell line (ATCC). A subpopulation of cells stably transfected with the plasmids was later obtained by the G418 antibiotic selection. Single cell clones were isolated from the mass population of stable transfectants using a limited dilution cloning strategy. A single clone with the highest reporter activity was used for a proof-of-concept study using known inhibitors of HIF. These inhibitors are the commercially available drugs, Bortezomib (Velcade) and Cisplatin.

The 4XEPO-HRE-FLuc plasmid construct contained four copies of the HRE of the EPO gene while the pcDNA3 vector carries a neomycin-resistant gene. Co-transfection of these plasmids into Saos-2 cells was performed at a 10:1 ratio (4XEPO-HRE-FLuc:pcDNA3) using the Lipofectamine 2000 (Invitrogen) fusogen. Initially, $8.3 \times 10^5$ Saos-2 cells were seeded in an antibiotic-free DMEM with 10% FBS in a T-25 flask for 24 hours. On the following day, a plasmid mixture was prepared by adding 11.4 µg of 4XEPO-HRE-FLuc and 1.14 µg of pcDNA3 in 625 µl serum-free and antibiotic-free DMEM. At the same time a transfection reagent mixture was prepared by adding 18.75 µl of Lipofectamine 2000 into 606.25 µl serum-free and antibiotic-free DMEM. The reagent mixture was gently mixed and incubated at room temperature for 5 minutes. After the incubation, the plasmid mixture and the reagent mixture were combined, vortexed and incubated at room temperature for 20 minutes. While the complexes were incubating, cultured media from the overnight T-25 flask Saos-2 cells was discarded, and the cells were washed once with 5 ml of serum- and antibiotic-free DMEM. At the end of the 20 minutes incubation, the 1250 µl of plasmid-Lipofectamine 2000 complexes was added into the cells. The flask was then swirled followed by an addition of 3750 µl of serum- and antibiotic-free DMEM. The cells were incubated for 6 hours in a humidified incubator supplied with 5% CO2 at 37° C. Five ml of DMEM with 10% serum and antibiotic-free was added into the flask after 6 hours in order to make a final concentration of 5% reduced-serum DMEM. Five ml of antibiotic-free DMEM with 10% FBS was then added into the in order to make final concentration of 5% reduced-serum DMEM.

Selection of a stably-transfected population of Saos-2 cells from the transfected cells above was performed using the G418 antibiotic. After 48 hours of incubation, the transfection media mixture was removed from the cells. They were then washed twice with 1×PBS followed by the addition of DMEM containing 1 mg/ml G418 and 10% FBS. The cells were continued to be incubated in a humidified incubator supplied with 5% CO2 at 37° C. for 3 more days. After the incubation period, spent media was removed and replaced with fresh media containing 1 mg/ml G418 and 10% FBS was added. This media replacement was done at every 3 days for a period of 3 weeks. After 3 weeks, the surviving cells, which constitute the mass population of stably-transfected, neomycin-resistant parental cells, were propagated further. This parental population was then tested for its ability to upregulate the luciferase reporter protein upon hypoxia induction.

To confirm the HIF reporter activity of neomycin-resistant parental population, a single luciferase assay was conducted. Initially, $2.5 \times 10^4$ of the cells were plated in wells of a 48-well plates in antibiotic-free DMEM with 10% FBS for 16 hours. One of the plates was then incubated for 24 hours in a normoxic (21% O2) gaseous atmosphere in a humidified CO2 incubator while the other was incubated in a hypoxic (0.5% O2) gaseous environment in a hypoxic chamber (BioSpherix, USA) controlled by an oxygen regulator (ProOx model 110, BioSpherix, USA. After 24 hours of exposure to different oxygen concentrations, Bright-Glo™ Luciferase Assay (Promega, USA) was conducted to analyse the HIF reporter activity. Initially, growth media in each well was discarded and the cells were rinsed once with 300 µl of 1×PBS. Room temperature-equilibrated Glo Lysis Buffer (GLB; 60 µl) was then added into the wells. Plates were then gently rocked on a shaker for 5 min at room temperature. Cell lysis was confirmed visually by observing the wells of the 48-well plate under a light microscope. Thirty microliters of the resulting cell lysates were then transferred into individual glass vials. Bright-Glo™ Assay Reagent was then added into each tube at a 1:1 (v/v) ratio. Luminescence intensity was immediately read and recorded by a Luminometer (Sirius-2, Titertek-Berthold).

After confirmation of the HIF reporter activity in the mass population of the stable parental neomycin-resistant cells, single cell cloning was performed using a limiting serial dilution cloning strategy. The parental cells were seeded in the first row wells (A1-A8) of a 96-well plate at $1.5 \times 10^4$ cells for 24 hours. After an overnight incubation, spent media in the wells was pippeted out carefully and the cells were washed with 50 µl 1×PBS. Trypsinization of cells was done by adding 50 µl of 1× Trypsin-EDTA in each well for 1 minute at 37° C. After cells became detached, the content of each well was topped up to 100 µl with DMEM supplemented with G 418 and 10% FBS. One hundred microliters of the same media was pipetted into the remaining 9 rows of empty wells. Cell suspension from the first well (100 µl) was then transferred into the adjacent well and the mixture was pipetted up and down. The same volume of cell suspension was then transferred from this well to the next. This process was repeated to obtain a two-fold serial dilution of the cell suspension. All of the cell suspension from the last well (200 µl) was diluted in 10 ml of conditioned DMEM supplemented with G 418 and 10% FBS. The mixture was then inverted up and down to ensure even distribution of cells. This cell suspension (100 µl) was aliquoted into wells of a 96-well plate. The plate was then incubated in a 45° slanted position for 5 hours at 37° C. This was done to ensure attachment of single cells at the edge of each respective well. After the incubation each well was examined for the presence of a single attached cell. Wells containing single cells were properly labeled. The plate was subjected to further incubation at 37° C. for 7 to 14 days. Individual cells in the wells were visualized only every 4 days to reduce disturbance of the cell culture media. During visualization, images of the cells were captured.

Single cells which survived and grew into a colony after the 7 to 14 days incubation were trypsinized and transferred into wells of a 48-well plate. As the number of cells gradually increased the subculturing was performed into bigger tissue culture containers. Parameters for the propagation and upscaling of the cells are summarized in Table 1. Each cell clone population was then cryopreserved for long term storage.

TABLE 1

Parameters for single cell clone upscaling.

| Type of Seed Vessel | Surface Area (cm$^2$) | 1XPBS | 1XTrypsin-EDTA | DMEM with G 418 and 10% FBS |
|---|---|---|---|---|
| 96-well plate | 0.37 | 0.05 | 0.03 | 0.1 |
| 48-well plate | 0.95 | 0.2 | 0.05 | 0.3 |
| 24-well plate | 1.65 | 0.5 | 0.1 | 0.5 |
| 6-well plate | 9.46 | 1 | 0.25 | 1 |
| T-25 flask | 25 | 3 | 0.5 | 5 |
| T-75 flask | 75 | 5 | 1 | 10 |

Volume (ml)

After pure stable cell clones were obtained, their reporter activity towards HIF induction was re-tested using the single luciferase assay as described above. The cells were also confirmed to be free from *mycoplasma* contamination using a 4'-6-Diamidino-2-phenylindole (DAPI) staining.

To determine the optimum cell density to be used in the HIF activity assay, $2.7 \times 10^4$, $3.3 \times 10^4$ and $4.0 \times 10^4$ cells were seeded into wells of a 48-well plate for 24 hours. The seeded cells were then exposed to either normoxic or hypoxic conditions for 24 hours, as described above. Following lysis and mixture with the Bright-Glo Assay Reagent, the bioluminescence intensity was analysed as described in the earlier methods.

To verify the property of the stable single cell population as an assay system to measure HIF activity, a proof of concept study was performed with commercially available and known HIF inhibitors. These inhibitors are Bortezomib (Velcade) and Cisplatin. Treatment of these drugs in certain cancer cells leads to cell death. To confirm that the inhibition of bioluminescence in our cell assay system is due to HIF inhibition rather than this cytotoxic effect, we simultaneously determined the viability of cells under various concentrations of each drug used for the inhibition assay. The 3-(4,5-dimethylthiazol-2-yl)-2,5-dimethyltetrazolium bromide MTT assay was used. Cells were seeded at $1.5 \times 10^4$ cells per well in 96-well plates for 24 hours followed by treatment with selected concentrations of Bortezomib and cisplatin. The cells were then incubated in either normoxic or hypoxic conditions for 24 hours. After the treatment, cell culture media was replaced with fresh serum-free DMEM containing 0.5 mg/ml MTT. After 4 hours of incubation in a humidified CO2 incubator at 37° C., formazan precipitates were dissolved with 100 µl of DMSO. The resulting reaction was read using a microplate reader at 570 nm absorbance and 630 nm as the reference wavelength. The half maximal inhibitory concentration (IC50) of each drug towards the cells was determined by plotting graphs using the Graphpad Prism 5 software. HIF inhibitory effects at the various concentrations of drugs tested were also measured using the single luciferase assay system. A correlation between the drugs' effects on cell viability and HIF inhibition was then evaluated.

EXAMPLE 2

Evaluation of the Screening System

Figure 2:
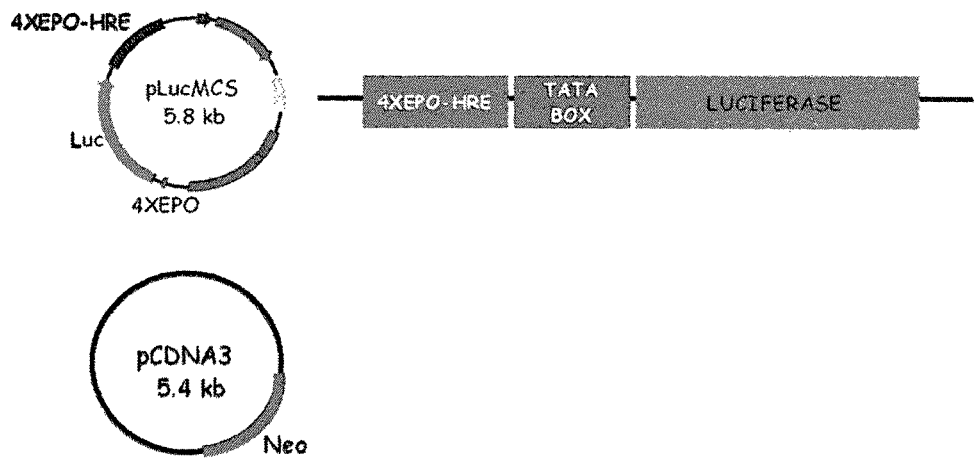
FIG. 2: Map of the plasmids that were co-transfected into Saos-2 cells.
Figure 3:
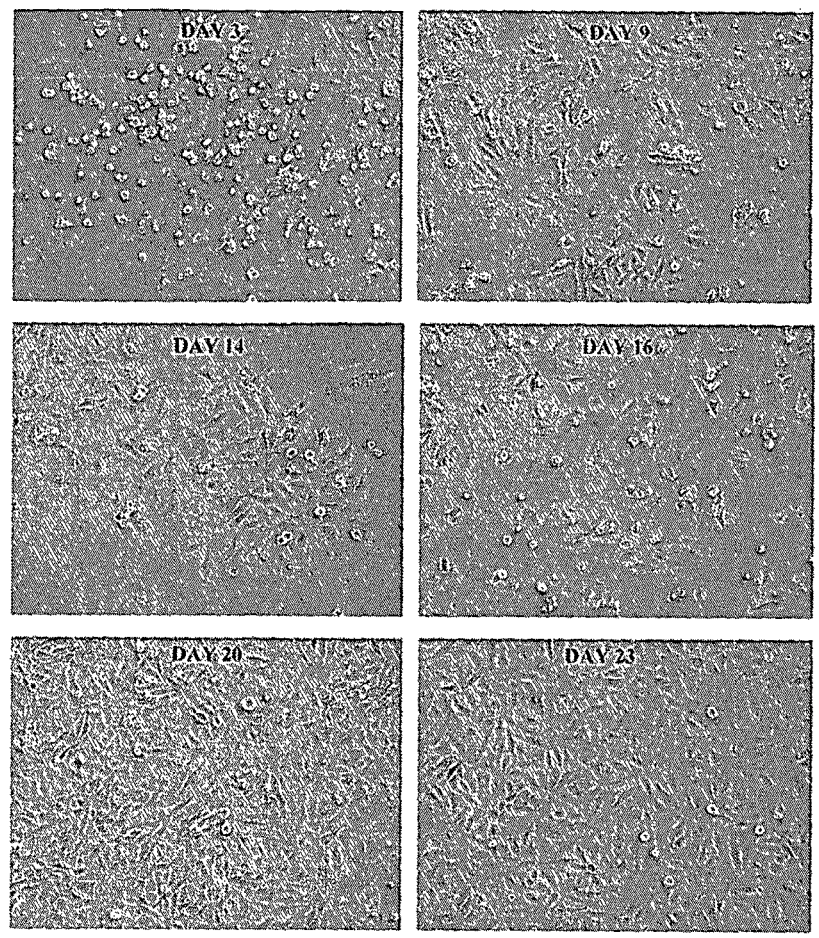
FIG. 3: Representative images of morphological changes in Saos-2 at different days following co-transfection with pLUC-MCS carrying the 4XEPO-HRE and pCDNA3 harboring the Neomycin resistant gene, and subsequent antibiotic treatment.

Saos-2 osteosarcoma cells, that showed a typical epithelioid morphology (FIG. 1), were co-transfected with the recombinant pLUC-MCS carrying the 4XEPO-HRE (4XEPO-HRE-FLuc) and pCDNA3 plasmids, harboring the Neomycin resistant gene (FIG. 2). The resulting transfectants were then treated with G418 antibiotics. Throughout the treatment, changes in the cell culture were monitored under a light microscope. Representative images of the observed morphological changes at selected times during the treatment are shown in FIG. 3. By day 3, most of the cells in the culture were rounded up and floating suggesting their sensitivity to the G418 treatment. Cells that appear to be resistant to the drug, on the other hand, continued to proliferate. After 20 days of treatment, this resistant population of cells became confluent in the tissue culture flasks. These cells, designated as the 'mass population', were propagated for further selection and stored for future use.

Figure 4:
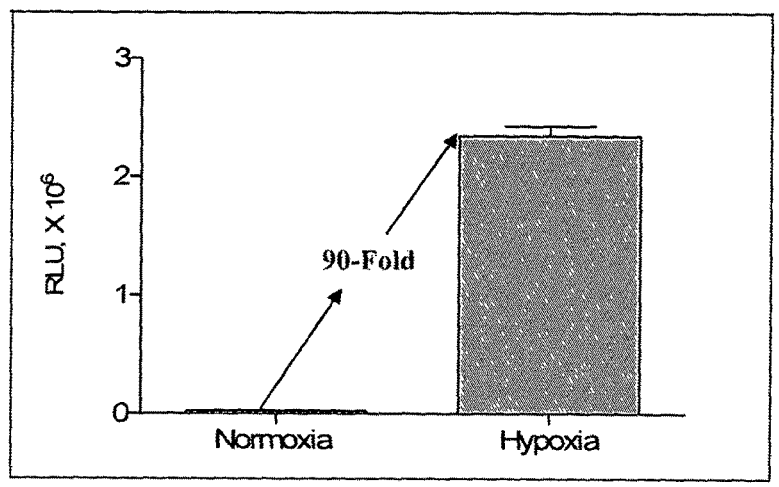
FIG. 4: Intensity of bioluminescence produced by the mass population of the stable transfectants upon hypoxia induction.

The mass population of cells was evaluated for their ability to respond to hypoxia stimulation by measuring their luciferase expression level. The hypoxic cells were found to be able to produce 90-fold higher luciferase signal compared to the cells in normoxia (FIG. 4). Therefore, we conclude that this mass population retained their 4XEPO-HRE gene construct, and they are responsive to hypoxia. A limiting serial dilution cloning strategy was then performed on these cells.

Figure 5:
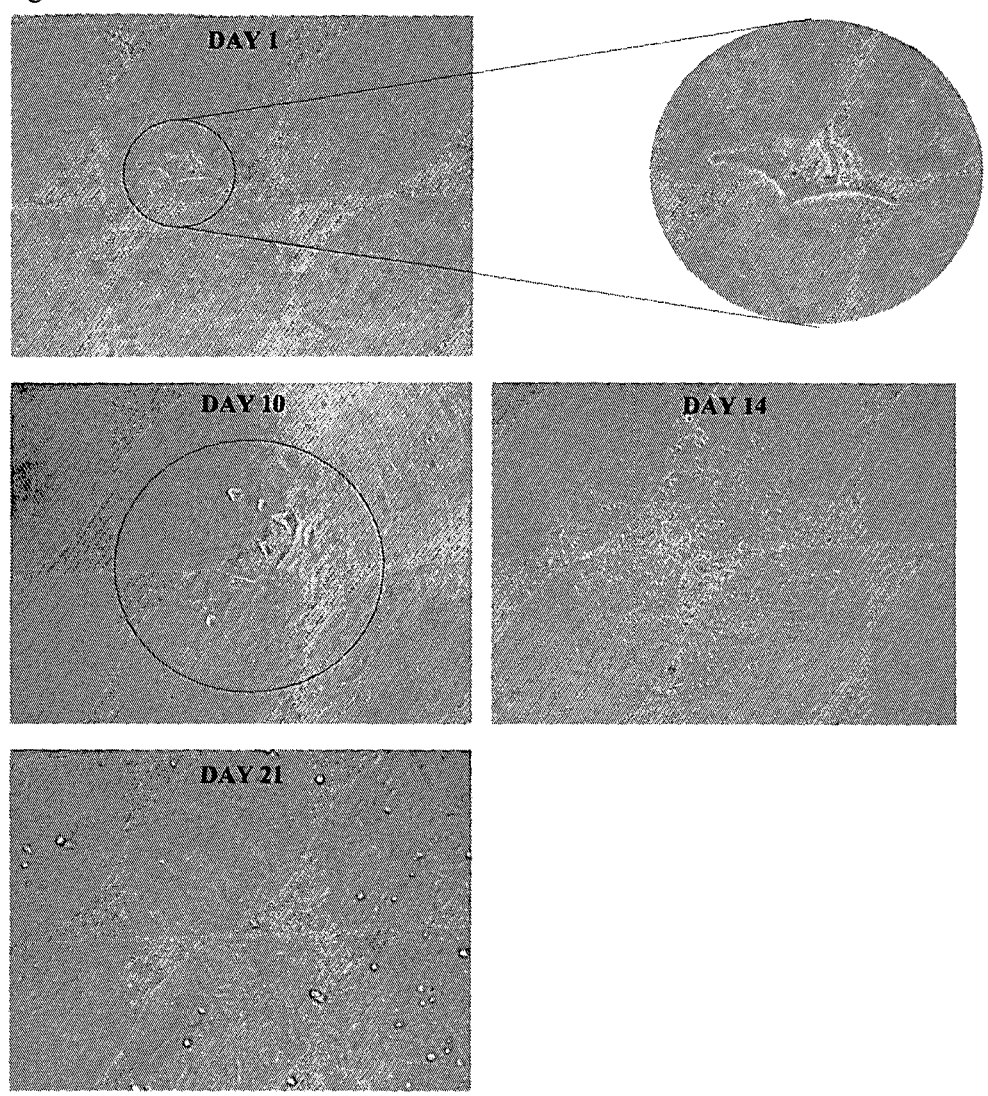
FIG. 5: Representative images for the development of a cell population from a single isolated cell.
Figure 6:
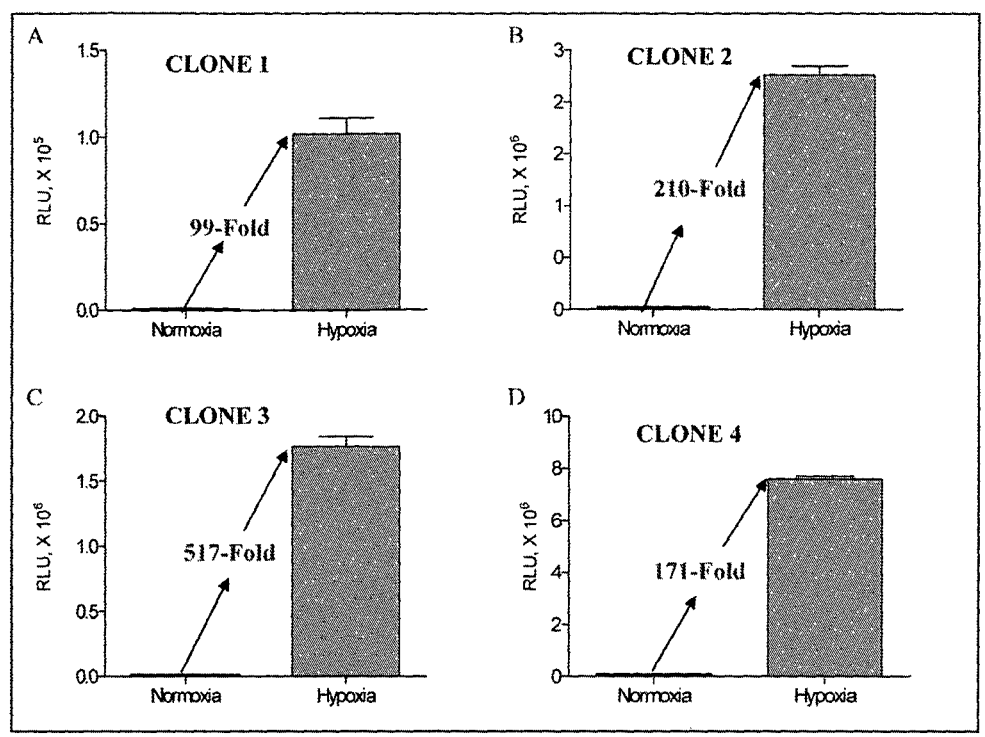
FIG. 6: Fold difference in bioluminescence intensity in each of the four clones upon hypoxia induction.

A number of single cells were obtained. Four of them proliferated to form cell colonies. Representative images of clone #3, at different times of the culture, are shown in FIG. 5. By day 21 each clone became a confluent population in the culture flask. To ensure that no *mycoplasma* contamination was introduced during the process, the cells were stained using DAPI staining method. Results obtained showed that they are free from contamination (FIG. 6).

Figure 7:
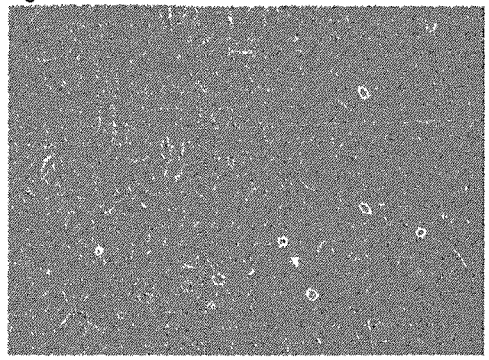
FIG. 7: Clone 3 cells displayed similar morphology to the parental Saos-2 cells following cultures in DMEM media with 10% FBS in a humidified CO2 incubator at 37° C.
Figure 8:
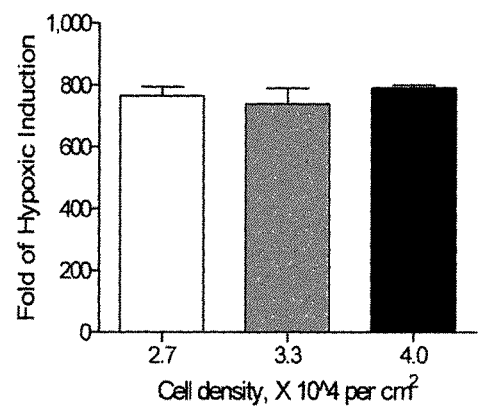
FIG. 8: Different cells numbers gave the similar fold difference in bioluminescense intensity following hypoxia induction.

To test the level of hypoxia-responsive luciferase signal of each cell clone, they were subjected to hypoxia exposure. All comparisons were done against their normoxia culture controls. Out of the four clones, clone 3 gave the highest luciferase signal, that was 517-fold higher than the normoxia control (FIG. 7). To the best of our knowledge, this is the highest hypoxia-specific signal that has been obtained thus far. Previously, using a VEGF promoter construct, Woldemichael et al., (2006) obtained a 40-fold signal intensity. Using a similar promoter, Bo et al., (2008) however only managed to obtain a 14-fold increase in signal. Even using a novel HIF reporter construct containing tandem repeats of minimum HIF binding sequences, Zhou et al., (2011) obtained just a 100-fold greater luciferase signal under hypoxia. Our clone 1 gave a fold difference comparable to their findings. However, our clones 2, 3 and 4 all gave a superior sensitivity. This increase in sensitivity will greatly improve the signal to noise ratio of various experimental conditions.

Figure 9:
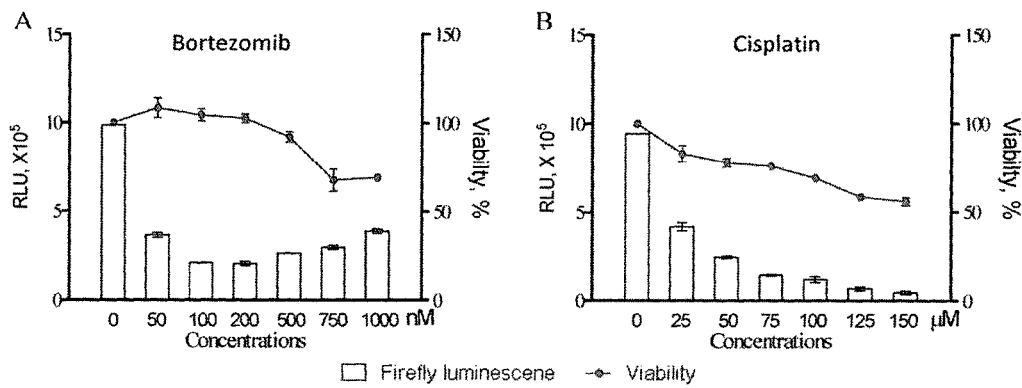
FIGS. 9A and B: Commercially available inhibitors of HIF activity, Bortezomib and cisplatin led to the reduction of reporter signal intensities.

Microscopic observation of all of the four stable Saos-2 clones showed no morphological differences compared to their parental cells (FIG. 7). High cell density is known to be a factor in increased HIF activity in certain cell lines (Kaluz et al., 2006). To test whether cell density affects the signal sensitivity of our clone 3, cells were cultured at different cell numbers and then exposed to hypoxia. Results showed that at densities of $2.7 \times 10^4$ to $4.0 \times 10^4$, no statistically significant variation was observed in the signals (FIG. 9). Hence, we conclude that the hypoxia-responsive signal produced by this stable Saos-2 clone remain consistent at different cell densities. We have also tested signal stability of the clone 3 as the passage numbers increased. Thus far, our findings showed that the signal intensity is still stable up to 30 passages (data not shown). We will monitor the signal further as the passage numbers increase over time.

A proof of concept study was conducted using known inhibitors of HIF which are Bortezomib and cisplatin. Bortezomib, a proteasomal inhibitor, was shown to inhibit transcriptional activity of HIF-1 via specific effect on HIF1-1α C-terminal activation domain (Kaluz et al., 2006). Treatment of bortezomib, at concentrations of up to 500 nM, significantly reduced the hypoxia-induced luciferase signal in our clone 3 cells without affecting cell viability (FIG. 10). At higher concentrations, the inhibition was associated with cell death. In addition to Bortezomib, cisplatin was also shown to inhibit HIF. The mechanism of inhibition, however, was achieved via a repression of HIF1-1α protein expression (Duyndam et al., 2007). In the present study, addition of cisplatin at 25 μM concentration led to almost 60% inhibition of luciferase signals in hypoxic clone 3. Viability of the cells was also reduced. Previous studies have shown that cisplatin treatment resulted in HIF inhibition and also apoptotic cell death (Tanaka et al., 2005). In summary, our proof of concept using Bortezomib and cisplatin showed that the hypoxia-inducible signal in our clone 3 population is responsive to the inhibitory effects of these drugs suggesting the reliability and sensitivity of the assay system.

REFERENCES

Duyndam M C, van Berkel M P, Dorsman J C, Rockx D A, Pinedo H M, Boven E. Cisplatin and doxorubicin repress Vascular Endothelial Growth Factor expression and differentially down-regulate Hypoxia-inducible Factor I activity in human ovarian cancer cells. Biochem Pharmacol. 2007 74:191-201.

Ek E T, Dass C R, Choong P F. Commonly used mouse models of osteosarcoma. Crit Rev Oncol Hematol. 2006 60:1-8.

Fogh J, Fogh J M, Orfeo T. One hundred and twenty-seven cultured human tumor cell lines producing tumors in nude mice. J Natl Cancer Inst 1977 59:221-6.

Ji D B, Zhu H B, Ye J, Li C L. Establishment of a cell-based sssay to screen regulators of the hypoxia-Inducible factor-1-dependent vascular endothelial growth factor promoter. Biol Pharm Bull 2008, 31: 2255-2259.

Rankin E B, Wu C, Khatri R, Wilson T L, Andersen R, Araldi E, Rankin A L, Yuan J, Kuo C J, Schipani E, Giaccia A J. The HIF Signaling Pathway in Osteoblasts Directly Modulates Erythropoiesis through the Production of EPO. Cell. 2012 149:63-74.

Kaluz, S., M. Kaluzova, and E. J. Stanbridge. The role of extracellular signal regulated protein kinase in transcriptional regulation of the hypoxia marker carbonic anhydrase IX. J Cell Biochem 2006, 97:207-16.

Keith B, Simon M C. Hypoxia-inducible factors, stem cells, and cancer. Cell. 2007 129:465-72.

Tanaka T, Kojima I, Ohse T, Inagi R, Miyata T, Ingelfinger J R, Fujita T, Nangaku M. Hypoxia-inducible factor modulates tubular cell survival in cisplatin nephrotoxicity. Am J Physiol Renal Physiol. 2005 289:F1123-33.

Woldemichael G M, Vasselli J R, Gardella R S, Mckee T C, Linehan W M, McMahon J B. Development of a cell-based reporter assay for screening of inhibitors of hypoxia-inducible factor 2-induced gene expression. J Biomol Screen 2006, 11: 678.

Zhou W, Dosey T L, Biechele T, Moon R T, Horwitz M S, Ruohola-Baker H. Assessment of hypoxia inducible factor levels in cancer cell lines upon hypoxic induction using a novel reporter construct. Plos One 2011, 6: e27460.

The invention claimed is:

1. A Saos-2 cell line that comprises stably integrated into its genome a gene construct consisting of a TATA box and a reporter gene integrated under the control of a hypoxia inducible factor (HIF) responsive promoter, wherein the HIF responsive promoter consists of four hypoxia-response elements (HREs) of the human erythropoietin (EPO) gene located in a tandem repeat, and wherein the HIF responsive promoter is upstream of the reporter gene.

2. A gene construct consisting of a TATA box and a reporter gene under the control of a hypoxia inducible factor (HIF) responsive promoter, wherein the HIF responsive promoter is at most 100 base pairs long and consists of four hypoxia-responsive elements (HREs) of the human erythropoietin (EPO) gene located in a tandem repeat; and wherein the HIF responsive promoter is upstream of the reporter gene.

3. The Saos-2 cell line, according to claim 1, wherein the reporter gene is firefly luciferase.

4. The gene construct, according to claim 2, wherein the reporter gene is firefly luciferase.

* * * * *